United States Patent [19]

Renth et al.

[11] 4,058,642
[45] Nov. 15, 1977

[54] 2-AMINO-3-(3'-HYDROXY-PHENYL)-PROPANOLS AND SALTS THEREOF

[75] Inventors: Ernst-Otto Renth; Anton Mentrüp; Kurt Schromm; Alexander Walland, all of Ingelheim am Rhein, Germany

[73] Assignee: Boehringer Ingelheim GmbH, Ingelheim am Rhein, Germany

[21] Appl. No.: 746,110

[22] Filed: Nov. 30, 1976

Related U.S. Application Data

[63] Continuation-in-part of Ser. No. 512,207, Oct. 4, 1974, abandoned.

[30] Foreign Application Priority Data

Oct. 11, 1973   Germany ............................ 2351027

[51] Int. Cl.$^2$ .................... A01N 9/20; A01N 9/24; C07C 91.22
[52] U.S. Cl. .................... 424/330; 260/141; 260/253; 260/343.5; 260/501.17; 260/501.18; 260/570.6; 260/600 R; 424/253; 424/316; 560/39; 560/40
[58] Field of Search .................... 260/570.6, 501.17; 424/316, 330, 253

[56] References Cited

U.S. PATENT DOCUMENTS 3,366,688   1/1968   Hargrove ............................ 260/584
3,804,899   4/1974   Ebnother et al. .................. 260/570.6

Primary Examiner—Robert V. Hines
Attorney, Agent, or Firm—Hammond & Littell

[57] ABSTRACT

Compounds of the formula

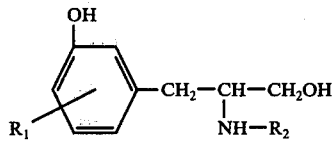

wherein
  $R_1$ is hydrogen, chlorine, hydroxyl, trifluoromethyl, methyl or methoxy, and
  $R_2$ is hydrogen, alkyl of 1 to 2 carbon atoms or benzyl;
and non-toxic, pharmacologically acceptable acid addition salts thereof; the compounds as well as the salts are useful as hypertensives.

8 Claims, No Drawings

2-AMINO-3-(3'-HYDROXY-PHENYL)-PROPANOLS AND SALTS THEREOF

This is a continuation-in-part of copending application Ser. No. 512,207 filed Oct. 4, 1974, now abandoned.

This invention relates to novel 2-amino-3-(3'-hydroxy-phenyl)-propanols and acid addition salts thereof, as well as to methods of preparing these compounds.

More particularly, the present invention relates to a novel class of propanol derivatives represented by the formula

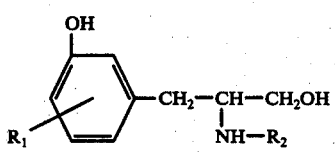

wherein
$R_1$ is hydrogen, chlorine, hydroxyl, trifluoromethyl, methyl or methoxy, and
$R_2$ is hydrogen, alkyl of 1 to 2 carbon atoms or benzyl;
and non-toxic, pharmacologically acceptable acid addition salts thereof.

A preferred subgenus thereunder is constituted by compounds of the formula I above, wherein
$R_1$ is hydrogen, chlorine, hydroxyl, methyl or methoxy, and
$R_2$ is hydrogen, methyl, ethyl or benzyl,
and non-toxic, pharmacologically acceptable acid addition salts thereof.

An especially preferred subgenus thereunder is constituted by compounds of the formula I above, wherein
$R_1$ is hydrogen, chlorine, 5-hydroxyl, methyl or methoxy, and
$R_2$ is hydrogen, methyl or ethyl,
and non-toxic, pharmacologically acceptable acid addition salts thereof.

The compounds embraced by formula I may be prepared by various methods utilizing known chemical synthesis principles, among which the following are preferred.

METHOD A

By reducing a compound of the formula

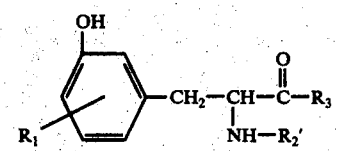

wherein
$R_1$ has the same meanings as in formula I,
$R_2'$ is alkanoyl of 1 to 4 carbon atoms, benzoyl or has the meanings defined for $R_2$ in formula I, and
$R_3$ is optionally substituted alkoxy,
with a complex hydride, such as lithium aluminum hydride, calcium borohydride, lithium borohydride, sodium borohydride or SDMA. When $R_2'$ in formula II is alkanoyl or benzoyl, the reducing action of the complex hydride simultaneously converts these acyl radicals to the corresponding hydrocarbyl radicals, provided a strong reducing complex hydride is used, such as lithium aluminum hydride or SDMA. On the other hand if a weaker reducing complex hydride is used, such as lithium borohydride or sodium borohydride, the amido group remains practically unaffected; in that case the alkanoyl or benzoyl substituent $R_2'$ is subsequently removed by conventional methods, so that ultimately a compound of the formula I wherein $R_2$ is hydrogen is obtained.

METHOD B

By removing one or more protective groups from a compound of the formula

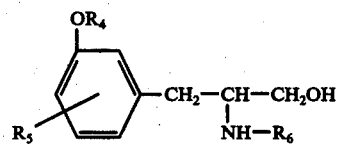

wherein
$R_4$ is hydrogen or a removable protective group for a phenolic hydroxyl substituent,
$R_5$ has the meanings defined for $R_1$ in formula I or is —$OR_7$, where $R_7$ is a removable protective group for a phenolic hydroxyl substituent, and
$R_6$ has the meanings defined for $R_2$ in formula I or is a removable protective group for an amino radical, which is removable by hydrogenation,
provided at least one of $R_4$, $R_5$ and $R_6$ is a removable protective group.

The protective groups $R_4$ and/or $R_7$ may be of the type which can be removed by hydrolysis, hydrogenation or ether cleavage, such as lower alkyl, benzyl or acyl. The removal of these protective groups may be effected by conventional methods. For instance, in the case of hydrolysis by means of aqueous acids or bases; the the case of hydrogenation by means of hydrogen in the presence of conventional hydrogenation catalysts, such as platinum, palladium or Raney nickel; and in the case of ether cleavage by means of hydrobromic acid, hydrochloric acid, borontrifluoride etherate, boron-tribromide or aluminum chloride.

The reaction products of the formula I obtained pursuant to the above methods are racemic mixtures and may, if desired, be separated into their optically active antipode components by conventional methods.

The compounds embraced by formula I are organic bases and therefore form acid addition salts with inorganic or organic acids. Examples of non-toxic, pharmacologically acceptable acid addition salts are those formed with hydrochloric acid, hydrobromic acid, acetic acid, propionic acid, maleic acid, citric acid, tartaric acid, 8-chlorotheophylline or the like.

The starting compounds required for methods A and B are either known compounds or may be prepared by known processes. For instance, the α-aminoacid esters of the formulas II and III may be obtained via the corresponding azlactones or by reaction of a correspondingly substituted benzyl halide with an acetamidocyanoacetic or malonic ester.

The following examples illustrate the present invention and will enable others skilled in the art to understand it more completely. It should be understood, however, that the invention is not limited solely to the particular examples given below.

EXAMPLE 1

2-Amino-3-(3',5'-dihydroxy-phenyl)-1-propanol hydrobromide by method B (a) 2-Amino-3-(3',5'-dimethoxy-phenyl)-1-propanol and its hydrochloride by method A 6.8 gm (28 millimols) of 3,5-dimethoxyphenyl-alanine methyl ester were dissolved in 35 ml of absolute tetrahydrofuran, and the solution was added dropwise to a stirred suspension of 3.2 gm (89 millimols) of lithium aluminum hydride in 35 ml of tetrahydrofuran at 20°–30° C. The resulting mixture was refluxed for two hours, then cooled and subsequently carefully admixed with water. The aqueous mixture was extracted with ethyl acetate, the organic phase was dried over sodium sulfate, and the solvent was distilled off in vacuo. The residue, 2-amino-3-(3',5'-dimethoxy-phenyl)-1-propanol, was admixed with the calculated amount of ethereal hydrochloric acid, yielding 6.5 gm (65% of theory) of the hydrochloride which had a melting point of 165° C.

(b) 4.5 gm (18.5 millimols) of the hydrochloride obtained in (a) were admixed with 45 ml of hydrogen bromide, and the mixture was refluxed for one hour. Thereafter, the excess, unreacted hydrogen bromide was distilled off in vacuo, the residue was freed from water by azeotropic distillation with toluene/ethanol, and the crystalline product thus obtained was recrystallized from isopropanol/ether, yielding 1.8 gm (37% of theory) of the compound of the formula

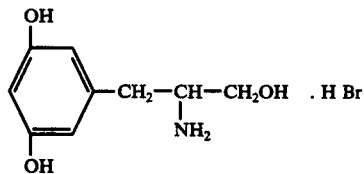

having a melting point of 118°–120° C.

EXAMPLE 2

2-Benzylamino-3-(3'-hydroxy-4'-methyl-phenyl)-1-propanol hydrobromide by method B (a) 2-Benzylamino-3-(3'-methoxy-4'-methyl-phenyl)-1-propanol and its hydrochloride by method A 55.5 gm (0.16 mol) of N-benzoyl-3-(3'-methoxy-4'-methyl-phenyl)-alanine ethyl ester (m.p. 133° C) were dissolved in 550 ml of absolute tetrahydrofuran, and the resulting solution was slowly added dropwise to a stirred suspension of 37 gm (0.98 mol) of lithium aluminum hydride in 1850 ml of tetrahydrofuran at room temperature in an atmosphere of nitrogen. The resulting mixture was refluxed for five hours, then allowed to stand overnight, and subsequently slowly admixed with water. The inorganic precipitate formed thereby was collected by vacuum filtration, washed with tetrahydrofuran, and the wash solution was combined with the filtrate. The tetrahydrofuran was distilled in vacuo out of the combined solution, the residue was taken up in ether, and the ethereal mixture was extracted with water. The ether phase was dried over sodium sulfate, the ether was distilled off, and the residue was recrystallized from petroleum ether, yielding 45.0 gm (97.5% of theory) of the free base 2-benzylamino-3-(3'-methoxy-4'-methyl-phenyl)-1-propanol.

The base was dissolved in ethyl acetate, and the solution was admixed with the calculated amount of ethereal hydrochloric acid, yielding 49.5 gm (95% of theory) of the hydrochloride which had a melting point of 191° C.

(b) 20 gm (62 millimols) of the hydrochloride obtained in (a) were admixed with 200 ml of 48% hydrobromic acid, and the mixture was refluxed for one hour. Thereafter, the reaction mixture was cooled, and the crystalline precipitate formed thereby was collected by suction filtration and recrystallized from water, yielding 21.5 gm (98.5% of theory) of the hydrobromide of the formula

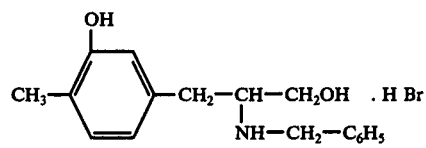

which had a melting point of 199° C.

EXAMPLE 3

2-Amino-3-(3'-hydroxy-4'-methyl-phenyl)-1-propanol hydrobromide by method B 21.5 gm (61 millimols) of 2-benzylamino-3-(3'-hydroxy-4'-methyl-phenyl)-1-propanol hydrobromide (see Example 2) were dissolved in 250 ml of methanol, 6 gm of 5% palladized charcoal were added to the solution, and the mixture was hydrogenated at 60° C and 5 atmospheres pressure. After the debenzylation had gone to completion, the reaction mixture was filtered, the methanol was distilled in vacuo out of the filtrate, the residue was dissolved in hot acetonitrile, and the solution was allowed to cool. The substance which crystallized out was collected by suction filtration and dried, yielding 13 gm (81.5% of theory) of 2-amino-3-(3'-hydroxy-4'-methyl-phenyl)-1-propanol hydrobromide having a melting point of 115°–117° C.

EXAMPLE 4

2-Amino-3-(3'-hydroxy-5'-methyl-phenyl)-1-propanol hydrobromide by method B (a) 3-(3'-Methoxy-5'-methyl-phenyl)-alanine, its ethyl ester, and their hydrochlorides 56 gm (0.33 mol) of 3-methoxy-5-methyl-benzyl chloride were added dropwise to a solution of 56 gm (0.33 mol) of ethyl acetamido-cyanoacetate and 7.8 gm of sodium in 330 ml of ethanol, and the resulting mixture was refluxed for four hours. Thereafter, the precipitated sodium chloride was separated by suction filtration, the ethanol was distilled in vacuo out of the filtrate, and the residue was hydrolized by boiling for 20 hours with 117 gm of potassium hydroxide in 920 ml of water. Thereafter, the reaction mixture was acidified with concentrated hydrochloric acid and then evaporated to dryness.

The aminoacid salt was extracted from the residue by treating it twice with one liter of ethanol each. The ethanolic extracts were combined, the ethanol was distilled off, and the residue was recrystallized from acetonitrile, yielding 46 gm (57% of theory) of 3-(3'-methoxy-5'-methyl-phenyl)alanine hydrochloride.

The ethyl ester was obtained with a yield of 65% of theory by azeotropic esterification; its hydrochloride had a melting point of 184°–185° C.

(b)
2-Amino-3-(3'-methoxy-5'-methyl-phenyl)-1-propanol hydrochloride by method A 33 gm of 2-amino-3-(3'-methoxy-5'-methyl-phenyl)alanine ethyl ester hydrochloride were suspended in ether and converted into the free base by addition of dilute ammonia to the suspension. The alkaline solution was dried over sodium sulfate, and then the ether was distilled off in vacuo. The residue was again dissolved in 330 ml of absolute ether, the resulting solution was added dropwise to a stirred suspension of 13.7 gm of lithium aluminum hydride in 700 ml of absolute ether, and the resulting mixture was refluxed for five hours. Thereafter, water was added, the mixture was suction filtered, and the filtrate was evaporated in vacuo. The residue, 2-amino-3-(3'-methoxy-5'-methyl)-1-propanol, was dissolved in acetonitrile, the resulting solution was admixed with the calculated amount of ethereal hydrochloric acid, and the precipitate formed thereby was collected by suction filtration and dried, yielding 23 gm (83% of theory) of the hydrochloride which had a melting point of 204°–205° C.

(c) 23 gm (0.1 mol) of the hydrochloride obtained in (b) were admixed with 230 ml of 48% hydrobromic acid, and the mixture was refluxed for one hour. Thereafter, some of the unreacted hydrobromic acid was distilled off, the residual mixture was cooled and then suction filtered, and the filter cake was recrystallized from aqueous acetonitrile, yielding 20 gm (76% of theory) of the hydrobromide of the formula

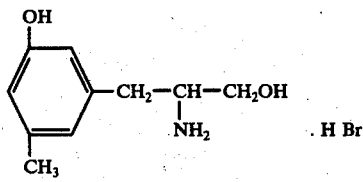

which had a melting point of 160° C.

EXAMPLE 5

2-Amino-3-(3'-hydroxy-4'-methoxy-phenyl)-1-propanol hydrochloride by method B 6 gm (18.6 millimols) of 2-benzylamino-3-(3'-hydroxy-4'-methoxy-phenyl)-1-propanol hydrochloride were dissolved in 60 ml of methanol, about 2 gm of 5% palladized charcoal were added to the solution, and the mixture was hydrogenated until the calculated amount of hydrogen had been absorbed. Thereafter, the catalyst was filtered off, the solvent distilled out of the filtrate in vacuo, and the residue was recrystallized from acetonitrile, yielding 4 gm (92% of theory) of the compound of the formula

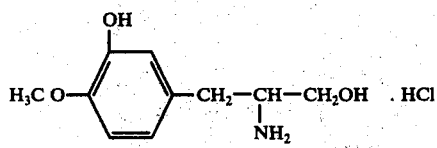

which had a melting point of 181°–182° C.

EXAMPLE 6

2-Amino-3-(3'-hydroxy-phenyl)-1-propanol hydrobromide by method B (a) 2-Amino-3-(3'-methoxy-phenyl)-1-propanol hydrochloride by method A 29 gm (0.139 mol) of 3-(3'-methoxy-phenyl)-alanine methyl ester were dissolved in 170 ml of absolute tetrahydrofuran, and the resulting solution was added dropwise to a stirred suspension of 10.6 gm (0.278 mol) of lithium aluminum hydride in 170 ml of absolute tetrahydrofuran. The resulting mixture was refluxed for 2 hours, and was subsequently worked up as described in the preceding examples, yielding 26.5% of theory of 2-amino-(3'-methoxy-phenyl)-1-propanol hydrochloride which had a melting point of 145° C.

(b) 8 gm of the hydrochloride obtained in (a) were admixed with 80 ml of 48% hydrobromic acid, and the mixture was refluxed for one hour. Thereafter, the reaction mixture was evaporated to dryness, the residue was stripped of water by entrainment with xylene, the solvent was distilled off, and the residue was recrystallized from ethyl acetate, yielding 6 gm (66% of theory) of the compound of the formula

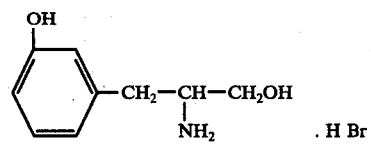

which had a melting point of 150°–152° C.

EXAMPLE 7

2-Amino-3-(3'-hydroxy-5'-trifluoromethyl-phenyl)-1-propanol hydrobromide by method B (a) 3-Methoxy-5-trifluoromethyl benzaldehyde 125 gm of 3-methoxy-5-trifluoromethyl-aniline were diazotized and then converted by the method of Beech (J. Chem. Soc. 1954, 1297) into 3-methoxy-5-trifluoromethyl-benzaldehyde, b.p. 58°–60° C at 0.1 mm Hg, $n_D^{20} = 1.4833$.

(b)
N-Benzoyl-3-(3'-methoxy-5'-trifluoromethyl-phenyl)alanine methyl ester

3-Methoxy-5-trifluoromethyl-benzaldehyde were reacted with hippuric acid to form the corresponding azlactone (m.p. 149°–150° C) which was converted into methyl α-benzamido-3-methoxy-5-trifluoromethyl-cinnamate (m.p. 143° C) by boiling in methanol in the presence of a catalytic amount of potassium carbonate, and the cinnamate catalytically hydrogenated to form N-benzoyl-3-(3'-methoxy-5'-trifluoromethyl-phenyl)-alanine methyl ester (m.p. 133° C).

(c)
2-Benzylamino-3-(3'-methoxy-5'-trifluoromethyl-phenyl)-1-propanol and its hydrochloride by method A 17 gm of the alanine ester obtained in (b) were reduced by the method described in Example 2(a) into the corresponding aminoalcohol whose hydrochloride had a melting point of 161° C.

(d)
2-Benzylamino-3-(3'-hydroxy-5'-trifluoromethyl-phenyl)-1-propanol hydrobromide by method B 15 gm of 2-benzylamino-3-(3'-methoxy-5'-trifluoromethyl-phenyl)-1-propanol hydrochloride were boiled with 48% hydrobromic acid for 1 hour. Thereafter, the reaction mixture was cooled, and the crystalline substance which had precipitated was collected by suction filtration and dried, yielding 11 gm of the above-named hydrobromide which had a melting point of 206°–207° C.

(e) In analogy to Example 3, the hydrobromide obtained in (d) was catalytically hydrogenated in methanol until the calculated amount of hydrogen had been absorbed, the catalyst was filtered off, the solvent was distilled out of the filtrate, and the residue was recrystallized from acetonitrile, yielding the compound of the formula

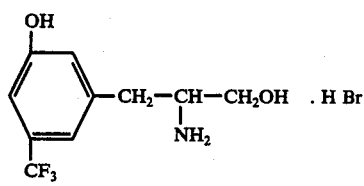

which had a melting point of 155°–156° C.

EXAMPLE 8

Using the synthesis steps described in Example 7, 2-amino-3-(2'-chloro-5'-hydroxy-phenyl)-1-propanol hydrobromide, m.p. 174°–175° C, of the formula

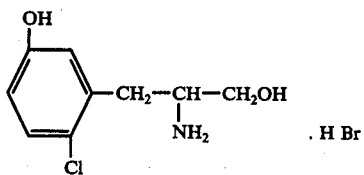

was prepared, starting from 2-chloro-5-methoxy-benzaldehyde, by condensation with hippuric acid to form the corresponding azlactone (m.p. 167° C), followed by conversion of the latter into the corresponding methyl hydrocinnamate (m.p. 121°–123° C), reduction of the ester with lithium aluminum hydride to form the hydrochloride of 2-benzylamino-3-(2'-chloro-5'methoxy-phenyl)-1-propanol (m.p. 167°–168° C), catalytic de-benzylation of the aminoalcohol to form 2-amino-3-(2'-chloro-5'-methoxy-phenyl)-1-propanol hydrochloride (m.p. 153°–155° C), and demethylation thereof with 48% hydrobromic acid.

EXAMPLE 9

2-Ethylamino-3-(3',5'-dihydroxy-phenyl)-1-propanol hydrobromide by method B (a) N-Acetyl-3-(3',5'-dimethoxy-phenyl)-alanine methyl ester 3,5-Dimethoxy-benzaldehyde was condensed with aceturic acid to yield 45% of theory of the corresponding azlactone (m.p. 142°–143° C), which was converted into N-acetyl-3-(3',5'-dimethoxy-phenyl)-alanine methyl ester (m.p. 110°–111° C) by refluxing in methanol in the presence of potassium carbonate and subsequent hydrogenation.

(b)
2-Ethylamino-3-(3',5'-dimethoxy-phenyl)-1-propanol hydrobromide by method A 42 gm of the methyl ester obtained in (a) were reduced with lithium aluminum hydride in absolute tetrahydrofuran to form 2-ethylamino-3-(3',5'-dimethoxy-phenyl)-1-propanol (m.p. 82°–83° C) whose hydrobromide had a melting point of 175° C.

(c) 10 gm of the hydrobromide obtained in (b) were demethylated by boiling with 48% hydrobromic acid out of the reaction mixture, the residue was recrystallized from acetonitrile, by yielding the compound of the formula

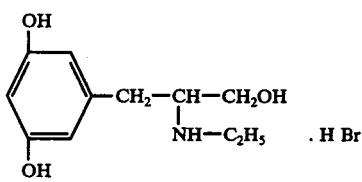

which had a melting point of 167°–168° C.

EXAMPLE 10

Analogous to Example 9, 2-methylamino-3-(3',5'-dihydroxy-phenyl)-1-propanol hydrobromide, m.p. 183°–186° C, was prepared by reducing N-formyl-3-(3',5'-dimethoxy-phenyl)alanine methyl ester with lithium aluminum hydride to form the hydrobromide of 2-methylamino-3-(3',5'-dimethoxy-phenyl)-1-propanol (m.p. 142° C), followed by de-methylation of the hydrobromide with 48% hydrobromic acid.

EXAMPLE 11

2-Amino-3-(3'-hydroxy-2'-methyl-phenyl)-1-propanol hydrobromide (a) N-Benzoyl-3-(3'-methoxy-2'-methyl-phenyl) methyl ester 3-Methoxy-2-methyl-aniline were converted into 3-methoxy-2-methyl-benzaldehyde by the method of Beech (see Example 7). The benzaldehyde was then reacted with hippuric acid to form the corresponding azlactone (m.p. 166° C), which was converted into N-benzoyl-3-(3'-methoxy-2'-methyl-phenyl)alanine methyl ester (m.p. 143°–144° C) by boiling with methanol/potassium carbonate, followed by catalytic hydrogenation.

(b) The alanine ester obtained in (a) was reduced with lithium aluminum hydride to form 2-benzylamino-3-(3'-methoxy-2'-methyl-phenyl)-1-propanol the hydrochloride of which had a melting point of 174° C. The hydrochloride was boiled with 48% hydrobromic acid to form 2-benzylamino-3-(3'-hydroxy-2'-methyl-phenyl)-1-propanol hydrobromide (m.p. 153° C), which was de-benzylated by catalytic hydrogenation, yielding the compound of the formula

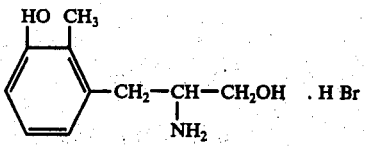

EXAMPLE 12

2-Amino-3-(3'-hydroxy-6'-methyl-phenyl)-1-propanol hydrobromide (a) N-Benzoyl-3-(3'-methoxy-6-methyl-phenyl)-alanine methyl ester 2,5-Cresotic acid was methylated with dimethyl sulfate to form 5-methoxy-o-toluic acid (m.p. 152°-154° C), which was converted into its acid chloride (b.p. 81°-83° C at 0.3 mm Hg), and the latter was reduced by the Rosenmund reduction [Berichte 51, 585 (1918)] into 5-methoxy-o-tolualdehyde (b.p. 75° C at 0.3 mm Hg). Thereafter, following the procedure described in Example 11, the aldehyde was converted into the corresponding azlactone (m.p. 170°-171° C), from which the N-benzoyl-3-(3'-methoxy-6'-methyl-phenyl)-alanine methyl ester (m.p. 98° C) was prepared.

(b) The ester obtained in (a) was reduced with lithium aluminum hydride to form 2-benzylamino-3-(3'-methoxy-6'-methyl-phenyl)-1-propanol, which was converted into its hydrochloride (m.p. 192°-193° C). The hydrochloride was de-methylated with 48% hydrobromic acid to form 2-benzylamino-3-(3'-hydroxy-6'-methyl-phenyl)-1-propanol hydrobromide, which was de-benzylated by catalytic hydrogenation, yielding the hydrobromide of the formula

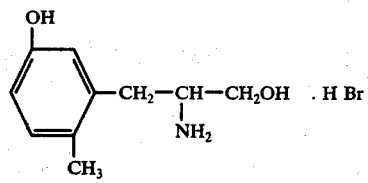

which had a melting point of 143° C.

EXAMPLE 13

2-Amino-3-(3',5'-dihydroxy-phenyl)-1-propanol hydrochloride (a) 2-Benzamido-3-(3',5'-dimethoxy-phenyl)-1-propanol 4.2 gm of sodium borohydride were added to a stirred mixture of 34.3 gm of N-benzoyl-3-(3',5'-dimethoxy-phenyl)alanine methyl ester and 350 ml of tetrahydrofuran at room temperature, the resulting mixture was stirred for 30 minutes more at room temperature, and then it was refluxed for five hours. After cooling of the reaction mixture, the solvent was distilled off in vacuo, the residue was suspended in water, and the suspension was acidified with acetic acid. The crystalline precipitate formed thereby was collected by suction filtration, washed with water, dried and recrystallized from toluene, yielding 2-benzamido-3-(3',5'-dimethoxy-phenyl)-1-propanol having a melting point of 117°-118° C.

(b) 21 gm of the end product obtained in (a) were added to 200 ml of 6 N hydrochloric acid, and the mixture was refluxed for eight hours. After cooling, the reaction mixture was extracted three times with chloroform, the aqueous phase was evaporated to dryness in vacuo, and the residue was recrystallized from glacial acetic acid, yielding the hydrochloride of 2-amino-3-(3',5'-dihydroxy-phenyl)-1-propanol having a melting point of 167° C.

EXAMPLE 14

2-Benzylamino-3-(3'-hydroxy-4'-methoxy-phenyl)-1-propanol and its hydrochloride 13 gm of N-benzoyl-3-(3'-hydroxy-4'-methoxy-phenyl)alanine methyl ester (m.p. 114°-116° C) were dissolved in 130 ml of absolute tetrahydrofuran, the solution was added dropwise to a stirred suspension of 9 gm of lithium aluminum hydride in 450 ml of absolute tetrahydrofuran, and the resulting mixture was refluxed for six hours. Thereafter, the reaction mixture was allowed to stand overnight, was then admixed with water, suction-filtered, and the filtrate was extracted twice with dimethylformamide at 60° C. The combined organic extract solutions were evaporated to dryness, the residue dissolved in 2 N hydrochloric acid, the resulting solution was extracted with ethyl acetate and the extract was then made alkaline again by addition of potash. The alkaline solution was dried over sodium sulfate, the solvent was distilled off in vacuo, the residue, 2-benzylamino-3-(3'-hydroxy-4'-methoxy-phenyl)-1-propanol, was dissolved in acetonitrile, the solution was admixed with the calculated amount of ethereal hydrochloric acid, and the precipitate formed thereby was collected by suction filtration, yielding 6 gm (47% of theory) of the hydrochloride of the formula

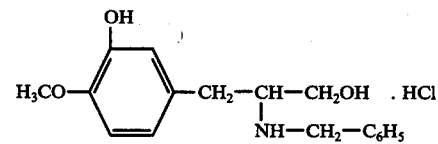

which had a melting point of 128° C.

EXAMPLE 15

2-Benzylamino-3-(3',5'-dihydroxy-phenyl)-1-propanol hydrobromide 15.7 gm (0.05 mol) of N-benzoyl-3-(3',5'-dihydroxyphenyl)-alanine methyl ester (m.p. 168° C) were dissolved in 200 ml of absolute tetrahydrofuran, and the solution was added slowly dropwise to a stirred suspension of 15.2 gm (0.4 mol) of lithium aluminum hydride in 600 ml of absolute tetrahydrofuran. The resulting mixture was refluxed for 3 hours and was then allowed to stand overnight at room temperature. Thereafter, the excess lithium aluminum hydride was decomposed by addition of water, the mixture was suctionfiltered, and the filter cake was extracted with warm dimethylformamide. The organic phase was evaporated in vacuo, the residue was dissolved in dilute hydrobromic acid, the solution was filtered through activated charcoal, and the filtrate was evaporated to dryness in vacuo, yielding 2-benzylamino-3-(3',5'-dihydroxy-phenyl)-1-propanol hydrobromide which had a melting point of 117°-119° C after recrystallization from acetonitrile.

The compounds of the present invention, that is, those embraced by formula I above and their non-toxic, pharmacologically acceptable acid addition salts, have useful pharmacodynamic properties. More particularly, they exhibit sympathomimetic properties, primarily hypertensive activity with long duration of effective action, in warm-blooded animals such as dogs and cats, and are therefore useful for enhancing the heart action and circulation.

The compounds of this invention are especially superior to related compounds with analogous pharmacological properties described in the prior art with respect to their duration of effective action. For example, the half-time of effective action of 2-amino-3-(3',5'-dihydroxy-phenyl)-1-propanol according to the present invention is about three times as long as the half-time of effective action of the known compound 1-(3'-hydroxy-phenyl)-2-ethylamino-ethanol.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from about 0.016 to 1.67 mgm/kg body weight, preferably 0.08 to 0.34 mgm/kg body weight.

The following examples illustrate a few pharamceutical dosage unit compositions comprising a compound of the present invention as an active ingredient and represent the best modes contemplated of putting the invention into practical use. The parts are parts by weight unless otherwise specified.

EXAMPLE 16

Tablets

The tablet composition is compounded from the following ingredients:

| 2-Amino-3-(3',5'-dihydroxy phenyl)-1-propanol hydrobromide | | 5 parts |
|---|---|---|
| Stearic acid | | 6 parts |
| Dextrose | | 589 parts |
| | Total | 600 parts |

Preparation

The ingredients are compounded in conventional manner, and the composition is compressed into 600 mgm-tablets in a conventional tablet making machine. Each tablet contains 5 mgm of the propanol compound and is an oral dosage unit composition with effective hypertensive action.

EXAMPLE 17

Suppositories

The suppository composition is compounded from the following ingredients:

| 2-Amino-3-(3',5'-dihydroxy-phenyl)-1-propanol hydrobromide | | 20 parts |
|---|---|---|
| Lactose, powdered | | 45 parts |
| Cocoa butter | | 1635 parts |
| | Total | 1700 parts |

Preparation

The cocoa butter is melted, the other ingredients are homogeneously blended into it, and 1700 mgm-portions of the mixture are poured into cooled suppository molds. EAch suppository contains 20 mgm of the propanol compound and is a rectal dosage unit composition with effective hypertensive action.

EXAMPLE 18

Gelatin Capsules

The capsule filler composition is compounded from the following ingredients:

| 2-Amino-3-(3',5'-dihydroxy-phenyl)-1-propanol hydrobromide | | 10 parts |
|---|---|---|
| Lactose | | 490 parts |
| Corn starch | | 400 parts |
| | Total | 900 parts |

Preparation

The ingredients are intimately admixed with each other, the mixture is pulverized by milling, and 900 mgm-portions of the milled composition are filled into gelatin capsules of suitable size. Each capsule contains 10 mgm of the propanol compound and is an oral dosage unit composition with effective hypertensive action.

Analogous results are obtained when any one of the other compounds embraced by formula I or a non-toxic acid addition salt thereof is substituted for the particular propanol compound in Examples 16 through 18. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A racemic mixture or optically active antipode of a compound of the formula

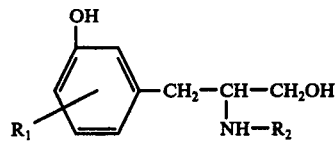

wherein
$R_1$ is hydrogen, chlorine, methyl, methoxy or 5-hydroxyl, and
$R_2$ is hydrogen, methyl or ethyl,
or a non-toxic, pharmacologically acceptable acid addition salt thereof.

2. A compound of claim 1, which is 2-amino-3-(3',5'-dihydroxy-phenyl)-1-propanol or a non-toxic, pharmacologically acceptable acid addition salt thereof.

3. A compound of claim 1, which is 2-benzylamino-3-(3'-hydroxy-4'-methyl-phenyl)-1-propanol or a non-toxic, pharmacologically acceptable acid addition salt thereof.

4. A compound of claim 1, which is 2-amino-3-(3'-hydroxy-4'-methoxy-phenyl)-1-propanol or a non-toxic, pharmacologically acceptable acid addition salt thereof.

5. A compound of claim 1, which is 2-amino-3-(3'-hydroxy-phenyl)-1-propanol or a non-toxic, pharmacologically acceptable acid addition salt thereof.

6. A compound of claim 1, which is 2-amino-3-(3'-hydroxy-5-trifluoromethyl-phenyl)-1-propanol or a non-toxic, pharmacologically acceptable acid addition salt thereof.

7. A hypertensive pharmaceutical dosage unit composition consisting essentially of an inert pharmaceutical carrer and an effective hypertensive amount of a compound of claim 1.

8. The method of increasing the blood pressure of a warm-blooded animal in need thereof, which comprises administering to said animal an effective hypertensive amount of a compound of claim 1.

* * * * *